United States Patent
Chandler

[11] Patent Number: 6,165,416
[45] Date of Patent: *Dec. 26, 2000

[54] SAMPLE COLLECTION DEVICE

[76] Inventor: Howard Milne Chandler, 857 Princes Point Rd., Yarmouth, Me. 04096

[ * ] Notice: This patent issued on a continued prosecution application filed under 37 CFR 1.53(d), and is subject to the twenty year patent term provisions of 35 U.S.C. 154(a)(2).

[21] Appl. No.: 08/913,393

[22] PCT Filed: Mar. 13, 1996

[86] PCT No.: PCT/AU96/00135

§ 371 Date: Nov. 26, 1997

§ 102(e) Date: Nov. 26, 1997

[87] PCT Pub. No.: WO96/28715

PCT Pub. Date: Sep. 19, 1996

[30] Foreign Application Priority Data

Mar. 14, 1995 [AU] Australia ................................. PN1737
Sep. 25, 1995 [AU] Australia ................................. PN5597

[51] Int. Cl.[7] ................................................ G01N 33/48
[52] U.S. Cl. .............................. 422/58; 422/61; 422/100; 422/104; 436/169; 436/178
[58] Field of Search ................... 422/56, 58, 61, 422/99, 101, 100, 102, 104; 436/164, 169, 177, 178

[56] References Cited

U.S. PATENT DOCUMENTS

| | | |
|---|---|---|
| 3,884,641 | 5/1975 | Kraffczyk et al. ..................... 422/61 |
| 4,789,629 | 12/1988 | Baker et al. ........................... 435/7 |
| 4,965,047 | 10/1990 | Hammond ............................ 422/58 |
| 4,981,653 | 1/1991 | Marino ................................. 422/56 |
| 4,981,786 | 1/1991 | Dafforn et al. ........................ 435/7 |
| 4,987,085 | 1/1991 | Allen et al. .......................... 422/58 |
| 5,100,619 | 3/1992 | Baker et al. ......................... 422/58 |
| 5,120,504 | 6/1992 | Petro-Roy et al. .................... 422/58 |
| 5,171,528 | 12/1992 | Wardlaw et al. ..................... 422/56 |
| 5,182,191 | 1/1993 | Fan et al. ............................ 435/7.9 |
| 5,238,847 | 8/1993 | Steinbiss et al. ..................... 436/64 |
| 5,504,013 | 4/1996 | Senior ................................. 436/165 |
| 5,523,055 | 6/1996 | Hansen et al. ....................... 422/61 |
| 5,639,424 | 6/1997 | Rausnitz ............................. 422/61 |
| 5,709,838 | 1/1998 | Porter et al. ......................... 422/61 |
| 5,962,336 | 10/1999 | Sun .................................... 422/58 |

FOREIGN PATENT DOCUMENTS 0 323 605   1/1994   European Pat. Off. .
WO 95/16207   6/1995   WIPO .

*Primary Examiner*—Lyle A. Alexander
*Attorney, Agent, or Firm*—Lahive & Cockfield, LLP

[57] ABSTRACT

A sample collection device (10), particularly for use in collection of faecal samples for occult blood detection, comprises a collection member having at least one absorbent matrix (12) thereon, and a protective cover member (14) for the collection member, the protective cover member being adapted to receive and shield at least the or each absorbent matrix of the collection member when the collection member is assembled therewith.

35 Claims, 7 Drawing Sheets

FIG 4A
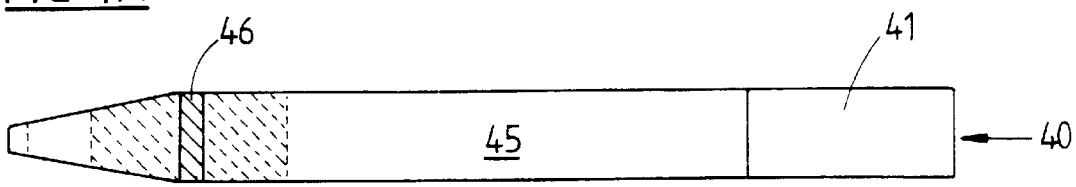
FIG 4B
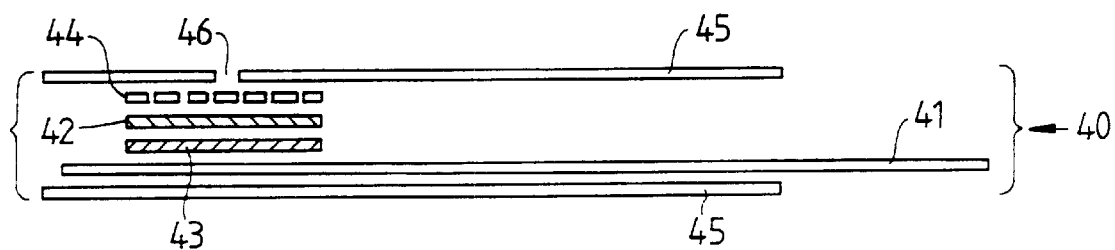
FIG 5A
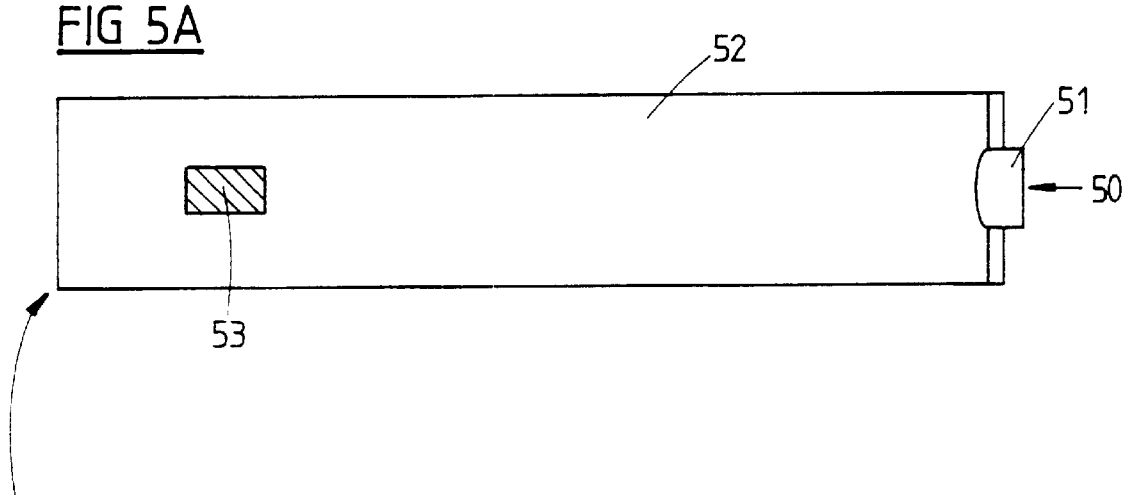
FIG 5B

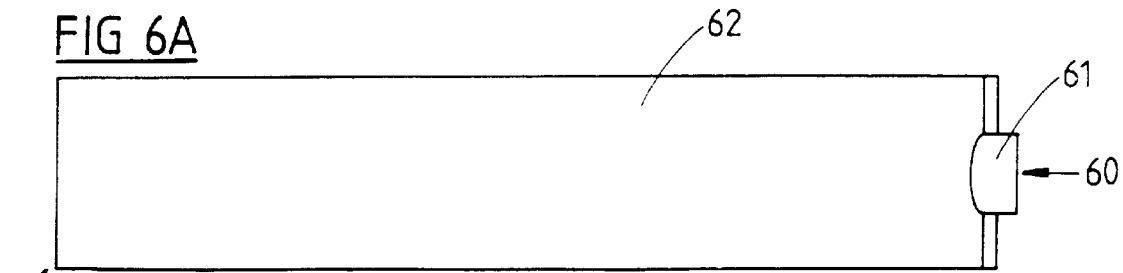
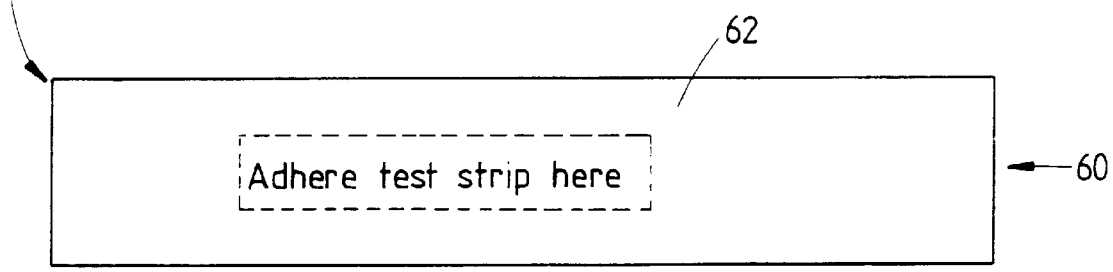
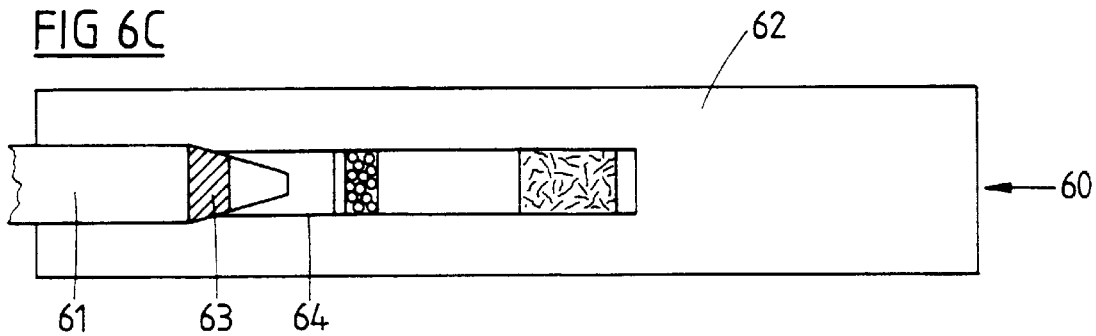

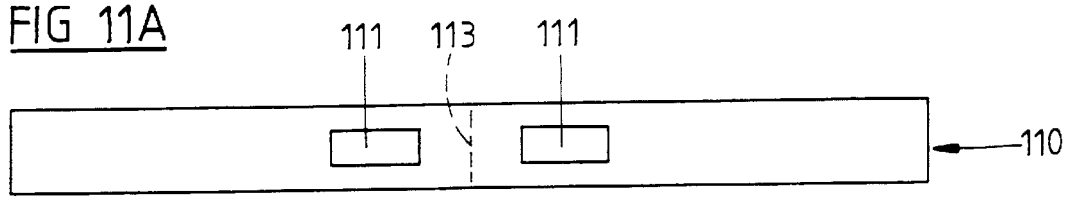
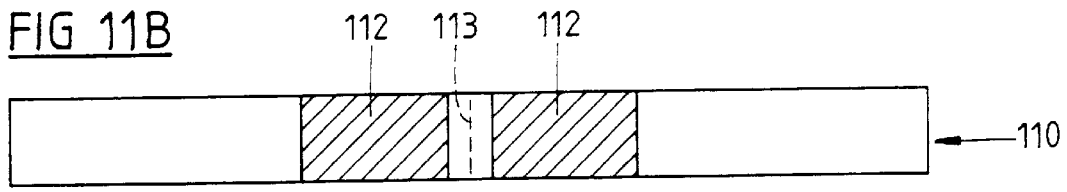
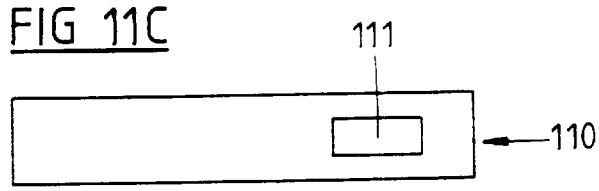
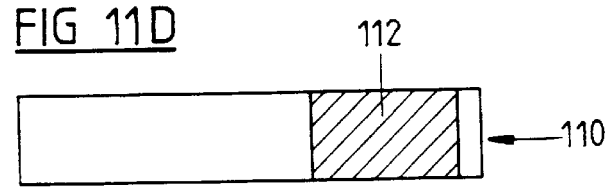

SAMPLE COLLECTION DEVICE

FIELD OF THE INVENTION

This invention relates to a device for collecting a sample, such as a biological sample, for subsequent use in the detection of an analyte in the sample. In one particular embodiment, this invention relates to a device for collecting a faecal sample for the purposes of subsequent occult blood detection in the sample. It is to be understood however that the device of this invention may be used in the collection of other biological samples such as blood, urine, saliva samples and the like, as well as in the collection of non-biological samples such as water samples for detection of pollutants and the like.

The present invention also extends to an assay device based on this sample collection device.

BACKGROUND OF THE INVENTION

A well known and widely-used clinical reagent for the detection of occult blood in a sample, particularly a faecal sample, is guaiac (also known as gum guaiac or resin guaiac). When used in association with an appropriate developer solution, guaiac provides a calorimetric assay system for detecting haemoglobin in the sample. Such tests are commercially available, for example, Hemoccult II and Hemoccult II Sensa (SmithKline Diagnostics, San Jose, Calif., USA).

Prior Australian Patent Application No. 21852/92 (International Patent Application No. PCT/US92/04425) notes that among the many analytical systems used for detection and/or determination of analytes, particularly analytes of biological interest, are chromatographic assay systems. Among the analytes of biological interest frequently assayed with such systems are:

1. hormones, such as human chronic gonadotropin (hCG), frequently assayed as a marker of human pregnancy;
2. antigens, particularly antigens specific to bacterial, viral, and protozoan pathogens, such as Streptococcus, hepatitis virus, and Giardia;
3. antibodies, particularly antibodies induced as a result of infection with pathogens, such as antibody to the bacterium *Helicobacter pylori* and to human immunodeficiency virus (HIV);
4. other proteins, such as haemoglobin, frequently assayed in determinations of faecal occult blood, an early indicator of gastrointestinal disorders such as colon cancer;
5. enzymes, such as aspartate aminotransferase, lactate dehydrogenase, alkaline phosphatase, and glutamate dehydrogenase, frequently assayed as indicators of physiological function and tissue damage;
6. drugs, both therapeutic drugs, such as antibiotics, tranquillisers and anticonvulsants, and illegal drugs of abuse, such as cocaine, heroin, and marijuana; and
7. vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such chromatographic systems are the "thin layer" systems in which a solvent moves as a solvent front across a thin, flat absorbent medium. Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time.

Chromatographic techniques used in conjunction with immunoassays include a procedure known as immunochromatography. In general, this technique uses a disclosing reagent or particle that has been linked to an antibody to the analyte to be assayed, forming a conjugate. This conjugate is then mixed with a specimen and, if the analyte to be assayed is present in the specimen, the disclosing reagent-linked antibodies bind to the analyte to be assayed, thereby giving an indication that the analyte to be assayed is present. The disclosing reagent or particle can be identifiable by colour, magnetic properties, radioactivity, specific reactivity with another molecule, or another physical or chemical property. The specific reactions that are employed vary with the nature of the analyte being assayed and the sample to be tested.

Although useful, currently available chromatographic techniques using test strips have a number of drawbacks. Many samples, such as faecal samples, contain particulate matter that can clog the pores of the chromatographic medium, greatly hindering the immunochromatographic process. Other samples, such as blood, contain cells and coloured components that make it difficult to read the test. Even if the sample does not create interference, it is frequently difficult with existing chromatographic test devices to apply the sample to the chromatographic medium so that the solvent front moves uniformly through the chromatographic medium to ensure that the sample reaches the area where binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as faeces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices, such as pipettes. Each of these devices is then contaminated and must be disposed of as waste using special precautions so that workers or people who may inadvertently come into contact with the waste do not become contaminated.

The present invention is particularly, but not exclusively, directed to collection of faecal samples for occult blood detection, for example in screening for colorectal cancer. As previously described, guaiac testing provides a calorimetric assay system for detection of haemoglobin in a sample, however because of the large number of false positives obtained in guaiac testing, in screening programs the use of two or three guaiac tests has been recommended, confirmed when positive by an immunological test for human haemoglobin (Favennic L., Kapel N., Meillet D., Chochillon C. and Gobert J. G., *Annales de Biologie Clinique*, 50(5):311–3, 1992). More recently, a combination of guaiac and immunological testing has been suggested (Allison, J. E., Tekawa, I. S., Ransom, L. J. and Adrian, L. L. *N. Engl. J. Med.*, 334:155–9, 1996).

It is an object of the present invention to provide a sample collection device which is simple and economic to manufacture and which enables subsequent detection and/or determination of analyte in the sample to be readily carried out, for example using an immunochromatographic or other immunodiagnostic procedure. It is a particular object of the present invention to provide a sample collection device which is suitable for use in testing for faecal occult blood in a combination of guaiac and immunological testing.

SUMMARY OF THE INVENTION

In accordance with the present invention, there is provided a sample collection device comprising
  (a) a collection member having at least one absorbent matrix thereon; and
  (b) a protective cover member for said collection member, said protective cover member being separate from said collection member and being adapted to receive and shield at least the absorbent matrix of said collection member when the collection member is assembled therewith.

In another aspect, the invention also provides an assay device for detection and/or determination of an analyte in a sample, comprising:
  (a) a collection member having at least one absorbent matrix thereon adapted to receive said sample,
  (b) a protective cover member for said collection member, said protective cover member being separate from said collection member and being adapted to receive and shield at least the or each absorbent matrix of said collection member when the collection member is assembled therewith, and
  (c) means to detect and/or determine said analyte in said sample.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Preferably, the collection member is an elongate member in the form of a dipstick, test strip or the like. Such an elongate collection member may comprise an elongate rigid or semi-rigid carrier or backing having the absorbent matrix affixed to the carrier or backing at or towards one end thereof. Typically, the elongate collection member may comprise a dipstick in the form of a flat, generally rectangular carrier strip, with the or each absorbent matrix being located at one end of the strip, and the opposite end of the strip providing means for handling the strip.

Suitable materials for use as a carrier or backing in such an elongate collection member include, for example, plastics materials such as polycarbonate, polyethylene, Mylar, vinyl, cellophane and polystyrene, as well as water-proofed or water-resistant cardboard or similar materials. In some embodiments of this invention, the carrier or backing is preferably made from a transparent or translucent material.

The or each absorbent matrix which is located on the collection member, preferably at or towards one end of a carrier strip, may comprise any suitable absorbent material. A particularly preferred material is absorbent paper such as filter paper, however any other absorbent material may also be used including, by way of example, cellulose, nitrocellulose, nylon, rayon, glass fibre, sintered glass, fleeces or non-woven or porous synthetic materials.

In one particular embodiment, the absorbent matrix on one or both sides of the collection member may comprise a sample collection matrix in operable contact with an absorbent reagent matrix or capillary means, so that reagent added to the absorbent reagent matrix or capillary means may flow along the collection member and into the sample collection matrix. If desired, at least the region of the junction between the sample collection matrix and the absorbent reagent matrix or capillary means may be covered with an impervious protective layer to prevent contamination of the absorbent reagent matrix or capillary means when a sample such as a faecal sample is applied to the sample collection matrix.

The absorbent matrix or matrices may be affixed to a carrier strip by means of an adhesive. Suitable adhesives are well-known in the art.

In order to assist in the collection of sample material, particularly faecal material, it is preferred that some means be provided for removal of excess sample material, particularly particulate material, after it has been applied to the absorbent matrix on the collection member. One such approach is to simply wipe the collection member with an absorbent material. Alternatively, a wiper sleeve of plastic backed absorbent paper or the like may be supplied on the collection member to clean away the excess material. In another embodiment, the collection member may be provided with an optionally removable protective cover layer or sheath which may be provided with a window or aperture whereby only the absorbent matrix or a portion thereof is exposed, so that after application of faecal material to the exposed portion of the absorbent matrix, the collection member may be removed from its protective sheath or the protective cover layer removed leaving excess faecal material to be disposed of with the cover layer or sheath, and the collection member may then be used in further testing as described herein.

Preferably, the protective cover member of the sample collection device of this invention is in the form of a sheath or housing having an internal recess which is adapted to receive the collection member and shield the absorbent matrix or matrices. In a particularly preferred embodiment the internal recess in the sheath or housing receives substantially the entire length of an elongate collection member.

The protective cover member is preferably made of a water-impervious, non-absorbent material. Suitable materials include plastics materials such as polycarbonate, and water-proofed or water-resistant cardboard or similar materials, as well as laminated materials such as plasticised cardboard or metal foil, for example plasticised aluminium foil. In one simple and inexpensive embodiment, the protective cover member may be made from a single flat piece of suitable material which is folded along one fold line to give two opposed panels which are then affixed at the edges, either with a suitable adhesive or by welding or fusing or the like, to form a sheath or housing with a suitable internal recess. In other embodiments, the initial piece of material may be folded along two or more fold lines to provide a sheath or housing as described above as a first opposable component together with one or more additional opposable components which are hingedly joined to the first opposable component and can be brought into opposition with the first opposable component during the test procedure.

In accordance with this invention, the protective cover member receives and shields at least the absorbent matrix or matrices of the collection member when assembled therewith. Thus, when a sample such as a faecal sample or other sample of biological interest is applied to the absorbent matrix or matrices and the collection member is assembled within the protective cover member, persons who handle the assembled device are protected against exposure to the sample and any bacterial, viral or protozoan pathogens which may be present in the sample.

In particular embodiments of the invention, the protective cover member may be provided with at least one window or aperture through a wall or panel thereof, the or each window or aperture being located so that it corresponds with at least a portion of an absorbent matrix when the collection member is assembled within the protective cover member. In these embodiments, the window or aperture enables test reagent(s) to be applied to a sample on the absorbent matrix during detection and/or determination of analyte(s) in the sample, without the need for removal of the collection device from the protective cover member. Such a window or aperture is preferably covered with a removable, and optionally resealable, sealing layer so that the window or aperture is covered by the sealing layer during collection and handling of the sample and then exposed so that test reagent(s) can be added to the sample when the test analysis is to be performed. Where the sealing layer is resealable, this layer can be reapplied to cover the window or aperture after the addition of the test reagent(s).

In further embodiments, one or more additional windows or apertures may be provided in the protective cover member. By way of example, such an additional window or aperture may be located so that, in conjunction with the use of a transparent or translucent carrier for the collection member, a reading window or aperture is provided for reading the results of a chromatographic test analysis through the transparent or translucent carrier. Once again, such additional windows or apertures may be covered with a sealing layer, which may be removable and resealable. Preferably, the sealing layer is transparent if the window or aperture is to be used to read test results.

The protective cover member may also include test reagent(s) sealed therein with a frangible seal, so that the test reagent(s) are released when the frangible seal is broken or perforated, for example on insertion of the collection member into the cover member.

In one embodiment of the sample collection device of this invention for use in faecal occult blood testing, at least a portion of the or each absorbent matrix on the collection member is impregnated with guaiac. In a particularly preferred embodiment for this use, the collection member is provided with two or more absorbent matrices and one of these is impregnated with guaiac, the other or others providing a sample taken simultaneously which is available for immunological testing.

Alternatively, or additionally, the sample collection device may further comprise a test strip located or adapted to be located on the collection member or on or in the protective cover member. Suitable test strips include a chromatographic medium, for example, immunochromatographic strips.

As previously described, the present invention also extends to an assay device which comprises, in addition to a collection member and a protective cover member as described above, means to detect and/or determine an analyte in the collected sample. Such means may include guaiac impregnated in the or each absorbent matrix, or alternatively or additionally a test strip (such as an immunochromatographic strip) located or adapted to be located on the collection member or on or in the protective cover member.

Various features of a number of embodiments of the present invention are illustrated by way of example in the accompanying drawings which are included by way of illustration, not limitation of this invention.

BRIEF DESCRIPTION OF THE DRAWINGS

In the accompanying drawings:

FIG. 4A is a plan view of a further embodiment of a dipstick collection device in accordance with this invention, and FIG. 4B is an exploded side elevation of the device of FIG. 4A.

FIG. 5A is a plan view from one side of an assembled sample collection device in accordance with a further embodiment of this invention which is particularly intended for use in the guaiac test for faecal occult blood, and FIG. 5B is a plan view of the reverse side of the sample collection device of FIG. 5A.

FIGS. 6A and 6B are plan views from opposite sides of a sample collection device in accordance with another embodiment of this invention which is particularly intended for use in immunodiagnostic testing for faecal occult blood, and FIG. 6C is a plan view of the device of FIGS. 6A and 6B in use in immunodiagnostic testing.

FIGS. 11A to 11D are plan views from opposite sides of a further embodiment of a sample collection device in accordance with this invention which is particularly intended for use in the guaiac test for faecal occult blood.

DETAILED DESCRIPTION OF THE INVENTION

Figure 1A:
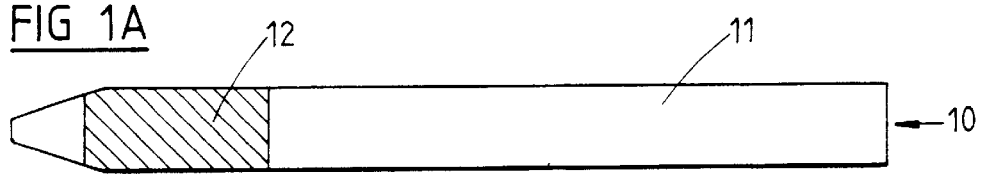
FIG. 1A is a plan view of a dipstick collection device in accordance with one embodiment of the present invention.
Figure 1B:
FIG. 1B is a side elevation of the device of FIG. 1A.
Figure 2:
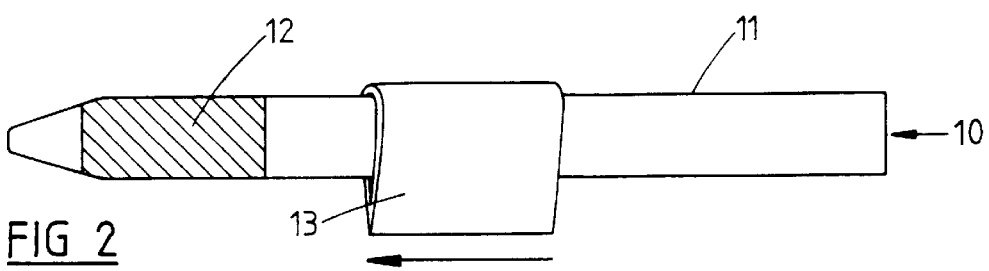
FIG. 2 is a plan view of a dipstick collection device in accordance with FIG. 1A, provided with a wiper sleeve as described below.

The dipstick collection device (10) shown in FIGS. 1A and 1B comprises a semi-rigid elongate backing (11) having an absorbent matrix (12) adhered to one side of one end of the backing (11). Alternatively, an absorbent matrix (12) may be located on each side of one end of the backing (11). As shown in FIG. 2, in use a wiper sleeve (13) may be used to wipe the dipstick (10) as the dipstick is withdrawn from the sleeve. The sleeve may be provided in the form of a preformed sleeve which may already be in place around the elongate semi-rigid backing (11).

Figure 10:
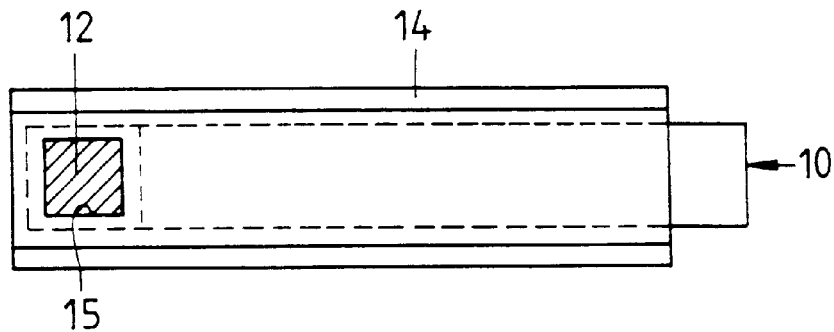
FIG. 10 shows diagrammatically an assembly of a dipstick collection device in a disposable protective sheath.

FIG. 10 shows an alternative embodiment in which the dipstick collection device (10) is provided within a disposable protective sheath (14) which may be made from paper, cardboard, plastic, foil or any other suitable material. The sheath (14) is provided with at least one opening (15) in registry with the absorbent matrix (12) of the device (10). Alternatively, if an absorbent matrix is provided on each side of the device (10), the sheath may be provided with an opening on each side thereof so that sample is collected on both sides of the dipstick device (10), thereby enabling two tests to be performed simultaneously or sequentially on the same sample. For example, both guaiac and immunochromatographic tests for faecal occult blood may be performed on the same sample. In use, the sheathed dipstick device is inserted into a faecal specimen so that a sample is applied, via the opening(s) in the base of the sheath, to the appropriate absorbent matrix region on one or both sides of the dipstick device. If desired, the openings may be covered with a screening or filter material to prevent the collection of particulate material. The sheath (14) is held while the dipstick device is withdrawn from the specimen, after which the sheath (14) is discarded with the excess faecal specimen. An alternative sheath (14) could be constructed of a biodegradable material such as paper or cardboard. The dipstick device (10) would be placed and held within the closed sheath (14) while the sample was taken. On withdrawal of the dipstick device, the sheath (14) would fall open for discarding, e.g. flushing, with the faeces.

Figure 3A:
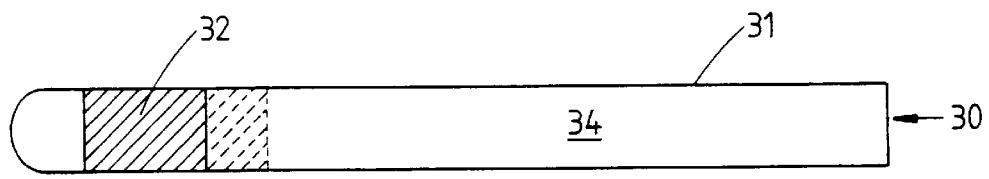
FIG. 3A is a plan view of another embodiment of a dipstick collection device in accordance with the invention.
Figure 3B:
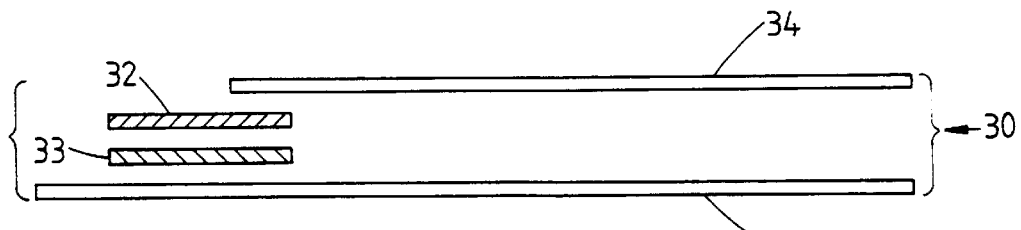
FIG. 3B is an exploded side elevation of the device of FIG. 3A.

FIGS. 3A and 3B illustrate another embodiment of a dipstick collection device (30) in which the absorbent matrix such as guaiac test paper (32) is adhered to one side and at one end of a transparent elongate backing (31) by means of a layer of double sided adhesive (33). A covering member (34) is laminated to the semi-rigid backing (31) in such a way that a portion of the absorbent guaiac test paper (32) is covered by the covering membrane (34), whilst the remainder of the guaiac test paper (32) is exposed for application of a test sample thereto.

A further embodiment of a dipstick collection device is shown in FIGS. 4A and 4B where the dipstick collection device 40 comprises a semi-rigid backing (41) having an absorbent collection matrix (42) adhered at one end thereof by means of double sided adhesive (43). Optionally, a filter screen (44) is provided over the absorbent collection matrix (42), and a peel-off impermeable cover (45) is provided over at least the end of the backing (41) where the absorbent collection matrix (42) is located. A gap (46) is provided in the impermeable cover (45) coincident with the absorbent collection matrix (42) (and filter screen (44) where provided) so that a sample such as a faecal sample applied to the impermeable cover can pass through the gap (46) and be collected by the absorbent collection matrix (42). The peel-off impermeable cover (45) may then be removed and discarded after sample collection so as to remove excess sample material from the dipstick collection device.

FIGS. 5A and 5B show an assembled sample collection device (50) in accordance with the present invention which is particularly intended for use in the guaiac test for faecal occult blood. Device (50) comprises a dipstick collection device (51) which may be a device of the type described in any one of FIGS. 1 to 4 or 10 above, together with a protective cover member or housing (52) which is adapted to receive and shield the absorbent matrix of the dipstick collection device when the collection device is assembled with the protective cover member. As shown in FIG. 5A, cover member (52) is provided with a window, aperture or perforations (53) through one side wall or panel thereof, the window, aperture or perforations being located to correspond with at least a portion of the absorbent matrix of the dipstick collection device (51) when the device (51) is assembled within the protective cover member or housing (52). As shown in FIG. 5B, the protective cover member or housing (52) may also be provided with a reading window (54) on the other side of the housing. The use of the device of FIGS. 5A and 5B in guaiac testing is described in detail below.

FIGS. 11A to 11D show another embodiment of a sample collection device for use in guaiac testing. FIGS. 11A and 11B show the device (110) from each side in "open" condition prior to faecal sample collection, while FIGS. 11C and 11D show the device (110) from each side in "closed" condition after sample collection. In current commercial guaiac tests for faecal occult blood, the faecal specimen is smeared on one side of the guaiac paper and the test reagent for development is applied to the reverse side of the guaiac paper. A similar approach is available in the embodiment of FIGS. 11A to 11D, which in addition allows two tests to be performed on the same faecal specimen.

FIG. 11A shows the "open" dipstick device (110) with the windows (111) side uppermost. FIG. 11B shows the opposite side of the "open" dipstick device (110) with guaiac paper (112) located near the fold in the elongate backing (113) of the device. FIG. 11C shows the dipstick device (110) folded ready for faecal collection, while FIG. 11D shows the dipstick device (110) folded in the reverse direction, with the faecal specimen hidden and the clean side of the guaiac paper exposed for addition of the test reagent(s).

The dipstick device (110), supplied folded as shown in FIG. 11C, is inserted or wiped with faecal specimen so that the guaiac paper exposed in the area of windows (111) both sides of the device (110) is contacted with specimen. The dipstick device is then cleaned (e.g. wiped with toilet tissue or a protective sheath/cover peeled off and discarded) so that faecal material remains only in the window area. The patient then folds the dipstick in the reverse direction as shown in FIG. 11D, inserts it into its protective cover member as described herein and sends it to the laboratory or health professional for development in the usual manner. If desired, a peelable or tearable seal may be provided along the edges of the device (110) in its folded condition as shown in FIG. 11C to prevent entry of faecal material to the guaiac paper (112) except through the windows (111).

FIGS. 6A and 6B illustrate a further embodiment of a sample collection device (60) in accordance with this invention which is particularly intended for use in immunodiagnostic testing for faecal occult blood, the device comprising a dipstick collection device (61) and a protective cover member or housing (62) adapted to receive and shield the dipstick collection device (61). As shown in FIG. 6B, an immunochromatographic test strip may be adhered to one side of the protective cover member (62) and used in the immunodiagnostic test by extraction of analyte from the absorbent matrix of dipstick collection device (61) by addition of an extraction reagent to the absorbent matrix (63) thereof, and then transferring the extraction reagent from the dipstick device (61) to the immunochromatographic test strip (64) as described in detail below.

Figure 7A:
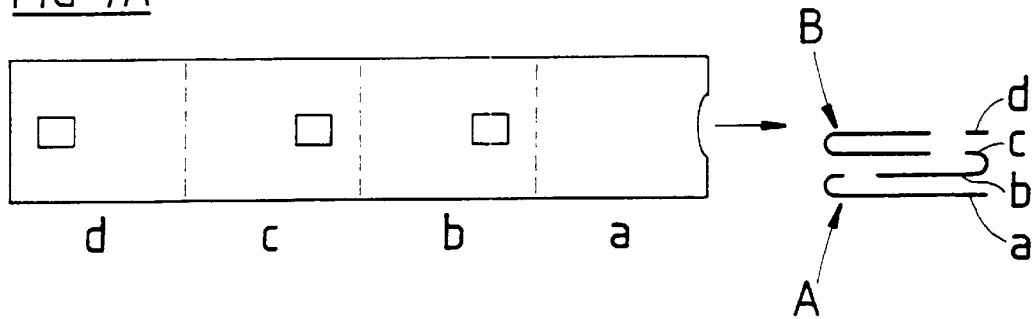
FIG. 7A is a diagrammatic illustration of the folding of a single piece of material such as cardboard to give a twopanel protective cover member for another embodiment of a sample collection device in accordance with this invention.
Figure 7B:
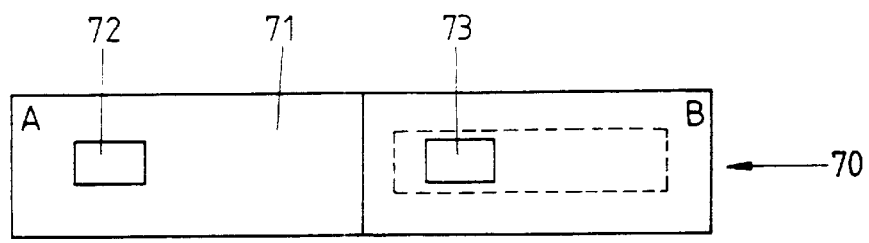
FIG. 7B is a plan view of the protective cover member of FIG. 7A in "open" position prior to insertion of the dipstick collection device.
Figure 7C:
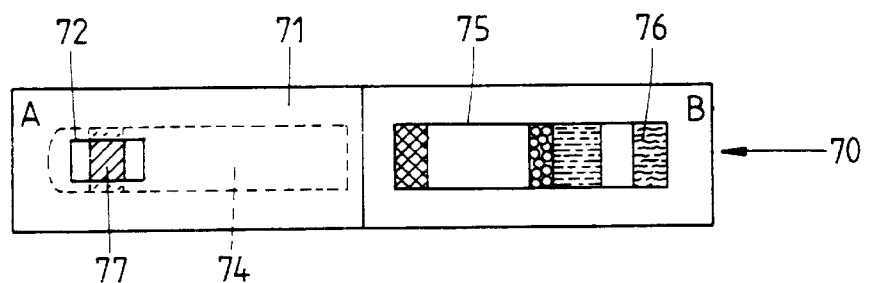
FIG. 7C is a plan view of the assembled sample collection device of FIGS. 7A and 7B for use in immunochromatographic testing.
Figure 7D:
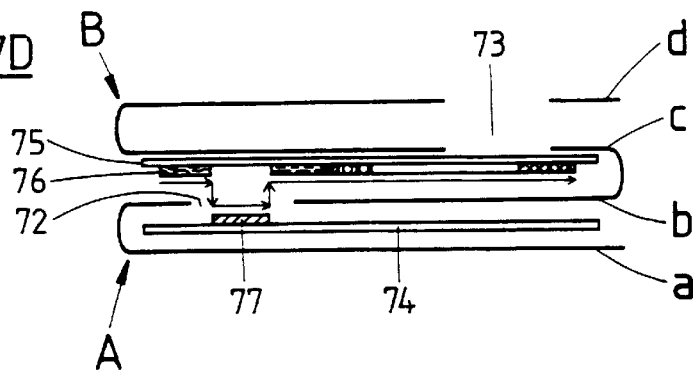
FIG. 7D shows diagrammatically the liquid flow paths between test strip and dipstick when a test is run using the device of FIGS. 7A and 7B.

FIGS. 7A, 7B and 7C illustrate an alternative embodiment of the protective cover member in accordance with this invention, with this embodiment being formed by folding a single piece of cardboard as shown in FIG. 7A to give a two-panel protective cover member (71). Member (71) is provided with apertures (72) and (73) in the panels thereof with aperture (72) being located so as to correspond with at least a portion of the absorbent matrix (77) of the dipstick collection device (74) when device (74) is assembled within panel A of the protective cover member (71). In use of the device shown in these figures, an immunochromatographic test strip (75) is located on panel B of the protective cover member (71) as illustrated in FIG. 7C, and extraction reagent is added to the reagent pad (76) at one end of the test strip and the protective cover member (71) closed. As described below, the extraction reagent flows from the reagent pad (76) along test strip (75) via the specimen matrix (77) of the dipstick (74) which it contacts through window (72) and then to the remaining components of the test strip, as is already well known. Since the test strip (75) is provided with a clear plastic backing, the result of the test can be observed through the window (73) in panel B.

Figure 8A:
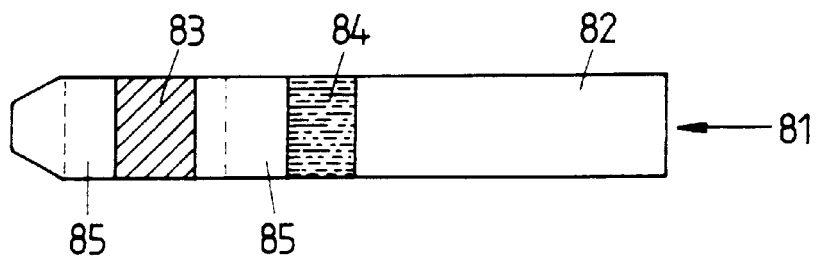
FIG. 8A is a plan view of a modified dipstick collection device of this invention.
Figure 8B:
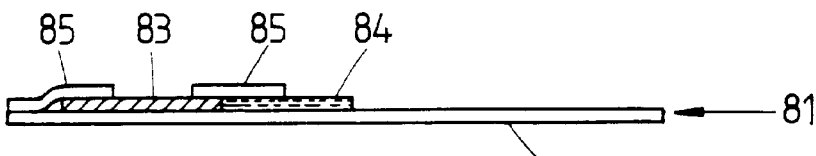
FIG. 8B is an exploded side elevation of the device of FIG. 8A.

The modified dipstick collection device (81) shown in FIGS. 8A and 8B comprises a semi-rigid elongate backing (82) having a sample collection matrix (83) adhered towards one end thereof, and in operable contact therewith an absorbent reagent matrix (84). An impermeable protective membrane layer (85) is provided which covers at least the junction between the sample collection matrix (83) and the absorbent reagent matrix (84) to prevent contamination of matrix (84) while still allowing test reagent(s) added to matrix (84) to flow along the device (81) and into the sample collection matrix (83).

As an alterative, absorbent reagent matrix (84) may be replaced by capillary means to conduct test reagent(s) to the sample collection matrix (83).

Figure 8C:
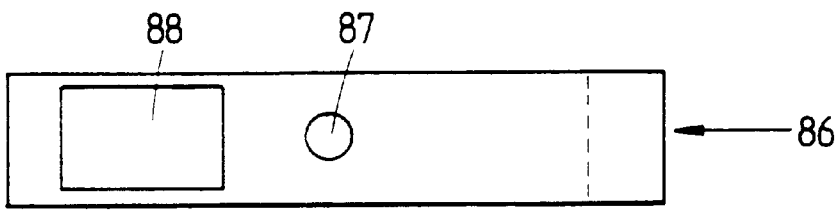
FIG. 8C is a plan view of a sheath for the dipstick collection device of FIG. 8A.

The protective cover member or sheath (86) shown in FIG. 8C is provided with a port or window (87) through which test reagent(s) may be applied to the absorbent reagent matrix (84) when the device (81) is received within the sheath (86), together with a transparent reading window (88) which registers with the sample collection matrix (83). Note that part of the sample collection matrix (83) may be covered by the protective membrane layer (85) to provide a clear region of the sample collection matrix for observing development of colour on the test paper.

Figure 9A:
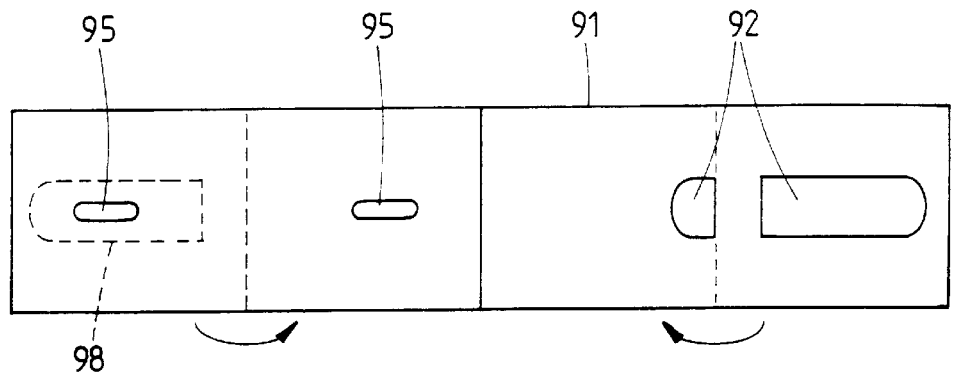
FIGS. 9A and 9B illustrate diagrammatically a further modification of the sample collection device of this invention.
Figure 9B:
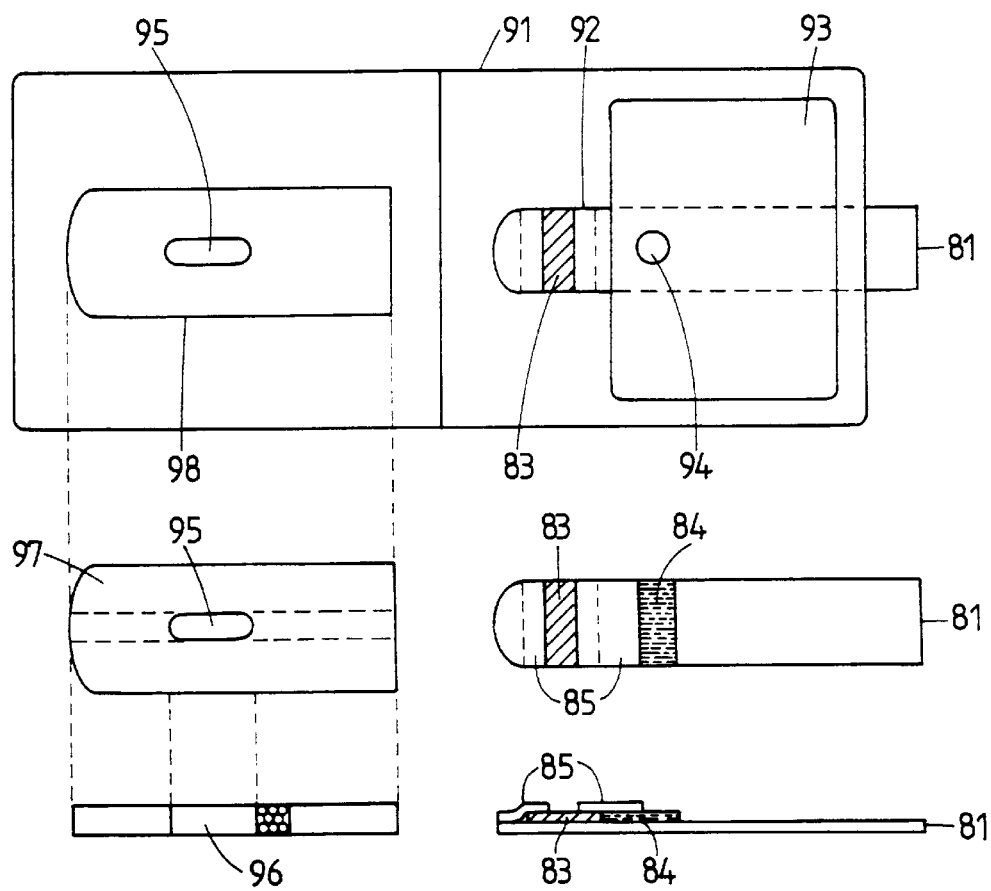

FIGS. 9A and 9B show a modified version of the sample collection device of FIG. 7, with the two-panel protective cover member (91) being formed by folding a single piece of cardboard, as shown in FIG. 9A. As shown in FIG. 9B, the sample collection device used in this modified version may be a modified dipstick device (81) as shown in FIGS. 8A and 8B, and described above.

In FIG. 9B, the right-hand panel of protective cover member (91) is provided with a recess (92) for insertion of dipstick device (81), and recess (92) is covered with a protective cover layer (93) which covers most of the dipstick device (81) when it is located within the cover member (91), but at least a portion of the sample collection matrix (83) is left exposed. A reagent port (94) is provided in the cover layer (93) for addition of test reagent(s) to the absorbent reagent matrix (84) of dipstick device (81). Window (95) is provided in the left-hand panel of cover member (91) to register with an immunochromatographic test strip (96). If desired, the test strip (96) may be mounted on a test strip insert (97) and a locating recess (98) provided in the left-hand panel of cover member (81) to ensure that, in use, test strip (96) is properly located with respect to both the dipstick device (81) and the window (95) through which the result of the test is to be observed.

The following detailed description relates to sample collection devices according to the present invention which are intended for faecal occult blood detection, both by guaiac and immunodiagnostic procedures. The collection devices of the invention have been developed with minimum-cost manufacture as the foremost consideration, but with ease and convenience of use as important secondary considerations. The devices are designed for manufacture by established high speed, fully automated commercial procedures, for example by web handling technology, and provide the basis for simple and inexpensive test kits.

Both collection devices use an elongate collection member referred to hereafter as a dipstick, as shown in FIGS. 1A and 1B. An absorbent matrix such as absorbent paper is adhered to one side of one end of a semi-rigid backing such as polycarbonate, Mylar, high impact polystyrene or waterproofed cardboard. In use, the dipstick is inserted into the faecal material and smeared to ensure complete and even penetration of the absorbent matrix by the specimen. Excess faecal material is then removed from the dipstick by one of several possible means. For example:

(i) the dipstick may simply be wiped clean by a suitable, readily disposable absorbent material such as toilet tissue;

(ii) plastic backed absorbent paper, such as used for covering laboratory benches, may be folded into a simple sleeve and used to wipe the dipstick clean as the dipstick is withdrawn from the sleeve. Alternatively, a pre-formed sleeve may be provided ready for use, or already in place around the stem of the dipstick (FIG. 2);

(iii) the dipstick may be supplied in a disposable, protective sheath which may be discarded with excess faecal material after sample collection (FIG. 10); or (iv) the dipstick may be manufactured with a peel-off impermeable cover (with or without a filter screen) as shown in FIGS. 4A and 4B, and after faecal collection, the cover is peeled-off and discarded.

Guaiac tests require dietary restrictions for several days before testing in order to avoid possible false positive results that may be caused by a number of foodstuffs and drugs. This limits the appeal and reliance that may be placed on this otherwise simple test. Immuno-based tests give specificity for human blood, but are more expensive and complex to perform.

These difficulties may be overcome by firstly performing mass screening using the guaiac test, but without dietary restrictions, and subsequently confirming guaiac positive specimens using an immunochromatographic test.

The "dipstick and sheath" approach of the present invention is ideal for this testing strategy, as one side of the dipstick may be provided with guaiac paper, the other with collection paper for an immuno-based test, both according to one of the several variations described herein. Alternatively, two dipsticks could be laminated together to achieve the same effect. Faecal specimen samples would thus be automatically collected simultaneously for both test types.

Upon identification of a guaiac-positive specimen, the dipstick containing the specimen would be removed from the sheath, turned over and the result confirmed by an immuno-test. This allows confirmation of the result on the same faecal specimen. As bleeding in many cases may be intermittent, performing confirmatory testing on later specimens may not be as useful.

1. Guaiac Testing.

Guaiac testing is the most widespread technology for faecal occult blood testing. The tests are rapid, inexpensive and easy to use, but lack specificity for human haemoglobin. Typically (e.g. SmithKline Diagnostics' Hemoccult), a faecal specimen is smeared on a test paper inside a test card and sent to the physician's office or laboratory for test development. Developer solution is added to the reverse side of the paper in the card and the development of a blue colour in the paper indicates a positive detection of haemoglobin. Some food materials (e.g. horseradish or haemoglobin from food animals) may cause false positive results with guaiac tests.

In using the collection device of this invention with guaiac procedures, the dipstick serves as both a collection and testing member, with the absorbent matrix being guaiac test paper. After the sample has been collected as described above, the test may be developed by the addition of developer solution to the test (guaiac) paper, and the result (blue colour development) read directly by observing the test paper or, if the dipstick has a transparent plastic carrier, indirectly through the carrier.

If desired, the dipstick may be provided with a covering membrane as shown in FIGS. 3A and 3B which is laminated to the semi-rigid backing in such a way that a portion of the guaiac test paper making up the absorbent matrix is protected from contact with the faecal sample. In use of such a device, developer solution added to the guaiac test paper is allowed to chromatograph away from the faecal sample and into the protected portion of the test paper, allowing development against a clear background and hence a clear region for observing the development of colour on the test paper.

In many cases, the collection of a sample may be done by a patient at home and the device handed to a physician and then sent to a laboratory for completion of the testing. In these cases, the wiped dipstick would be inserted into the paper, cardboard or plastic sheath or other protective cover member on which the patient's name, and possibly test instructions, could be written. Testing at the laboratory could then be completed by simply removing the dipstick from the sheath, adding developer solution and reading as described above.

Alternatively, the sheath may be constructed as shown in FIGS. 5A and 5B in order to protect the patient, physician and test operator from exposure to the faecal sample. In this case, the dipstick would have a clear plastic carrier backing and would be placed in the sheath or other protective cover member so that the guaiac test paper was located below an aperture in the sheath. The operator would add a drop of developer solution to the test paper via the aperture, and turn the sheath over to read the result via the reading window in the other side of the sheath. (For additional containment, the aperture may be covered with a resealable, peel-back sealing layer and, if desired, the window sealed with a clear sealing layer.)

In the modification shown in FIGS. 8A and 8B, the dipstick has been modified by the addition of an absorbent reagent matrix above, and in operable contact with, the sample collection matrix, such as guaiac faecal collection paper. The flow of test reagent is therefore changed along the dipstick. The region of the junction between the sample collection matrix and the reagent matrix is preferably covered with a protective membrane, which serves to protect the reagent matrix from faecal contamination. The protective membrane may also be printed to indicate the depth limit for faecal smearing, and the orientation of the dipstick for its insertion in the sheath.

One advantage offered by these modifications is that the absorbent matrix at the top of the sample collection matrix assists rapid drying of a faecal specimen. The moisture is drawn from the sample collection matrix by the absorbent and vented via the reagent port in the sheath. Rapid drying of the faecal specimen is important in order to avoid degradation of the analyte. The absorbent matrix may also be pre-impregnated with materials for removing or disguising any odours from the faecal specimen.

Addition of the test reagent to the absorbent matrix also ensures that its flow is controlled and that there is an orderly and even application of reagent to the top of the sample collection matrix. Furthermore, for guaiac testing, containment is improved as only the clean absorbent reagent matrix is exposed at the reagent addition port.

In this modified embodiment, the dipstick collection device may have a band of guaiac paper, with its lower region protected from faecal contact by a clear protective membrane. A band of absorbent material (e.g. Ahlstrom 1281 or 939 paper) is in operable contact with the upper margin of the guaiac paper. The upper margin of the guaiac paper and the lower region of the absorbent are covered with an adhesive membrane, which serves to protect the absorbent from faecal contact. Alternatively, the absorbent material may be replaced by a capillary device.

The protective cover member or sheath is also modified to allow reagent addition directly to the absorbent paper, which acts as a reservoir for orderly and even application of the developer to the guaiac paper. Preferably the sheath would be formed of a clear plastic material, so that the downward migration of the developer solution may be visualised in the guaiac paper, without exposure to the faecal-contaminated surface of the guaiac paper.

The sample collection device described above enables simple faecal occult blood testing kits to be made available particularly to developing countries and cost-sensitive markets. Such test kits may consist of bulk packaged dipsticks and sheaths, together with an appropriate supply of developer solution. Such test kits would significantly reduce the cost of guaiac testing for faecal occult blood since the dipstick uses minimal and inexpensive materials relative to current test systems, the dipstick may be manufactured by a continuous, high speed, low cost manufacturing process, whereas existing tests involve more manufacturing stages and greater complexity; insertion of the dipstick into the specimen reduces exposure to the specimen and avoids the requirement to include a smearing stick or paddle in the kit, and the small number of kit components and compact nature of the components ensures low packaging, transport and storage costs.

2. Immunodiagnostic Testing

Immunodiagnostic testing allows absolute specificity for human haemoglobin in faecal occult blood testing (e.g. SmithKline Diagnostics' HemeSelect), but entails some increase in test cost and complexity. In some markets, immunodiagnostic tests will be essential in order to avoid interference from commonly used foodstuffs. If available at a sufficiently low cost, these tests could ultimately replace guaiac tests.

For immunodiagnostic testing using the sample collection device of this invention, the dipstick may act simply as a collection instrument for subsequent transfer of faecal extract to an immunodiagnostic test device, or the dipstick may be used both for sample collection and, in conjunction with a protective sheath, as a test device. The absorbent matrix on the dipstick is a suitable collection paper (e.g. Whatman's #1) and the dipstick is inserted into the faecal material, removed, cleaned and sheathed in the protective cover member as already described. The faecal collection matrix may then be extracted immediately to yield a test sample, or sent to the physician's office or laboratory for subsequent extraction and completion of testing. There the dipstick may be unsheathed and the faecal material extracted from the collection matrix by the addition of one or more drops of extraction reagent, typically a buffered detergent solution such as PBS-Tween 20.

For example, extraction reagent may be added to the absorbent matrix with the collection device in the horizontal position. The reagent remains in contact with the matrix thereby allowing mobilisation of any haemoglobin into the reagent. The liquid extract may then be transferred from the dipstick to an immunodiagnostic test device by simply elevating the handle end of the dipstick and pouring the drop from the dipstick to the test device. The extract may be transferred to a microwell, tube or membrane for EIA testing, or to the sample port/specimen pad of an immunochromatographic device for "one-step" diagnostic testing. A suitable immunochromatographic device for diagnostic testing is described in Australian Patent Application No. 21852192 (International Patent Application No. PCT/US92/04425) referred to above, the contents of which are incorporated herein by reference.

A simple low-cost diagnostic kit, using the collection device of this invention and intended particularly for "cost-conscious" applications, is illustrated in FIGS. 6A, 6B and 6C.

The faecal specimen is collected on the absorbent matrix and the dipstick inserted into a sheath that has printed on it the patient's name, a marked position indicating the placement for an immunochromatographic test strip and the instructions for the test. The immunochromatographic test strips are packaged in bulk in a resealable container with sufficient desiccant to maintain dry conditions. A strip is taken from the container, protective paper removed from its underside to expose adhesive and the strip affixed via the adhesive to the position outlined on the sheath. The end of the dipstick where the absorbent matrix is located is placed in a horizontal position in contact with the sample receiving pad of the test strip. Extraction reagent is added to the absorbent matrix and the dipstick tipped to transfer the specimen extract to the test strip. With most immunochromatographic devices, the results typically develop in the test strip within five minutes.

A marginally more complex version of the kit, which offers improved containment of any pathogenic organisms in the sample, is shown in FIGS. 7A, 7B, 7C and 7D.

The sheath is formed from a single piece of cardboard, folded as shown in FIG. 7A to give a twopanel housing. The housing is shown in "open" form in FIGS. 7B and 7C and may be closed by folding the panels together prior to use.

The closed (spot glued) housing is issued to the patient who collects the specimen and inserts the dipstick into panel A, which acts as the sheath. The physician opens the housing and adheres a test strip to the position indicated in dotted outline on panel B. The extraction reagent is added to the reagent pad at the base of the test strip and the housing sealed closed. The liquid flowpath is as shown diagrammatically in FIG. 7D. The extraction reagent flows from the reagent pad, via the specimen matrix of the dipstick (thereby mobilising any haemoglobin), to the remaining components of the test strip. The test strip is on a clear plastic backing, which allows the result to be observed through the window of the closed housing.

This test format offers maximum containment and ease of use, and suitable devices for immunochromatographic testing utilising this test format are described in Australian Patent Application No. 21852/92, above.

FIGS. 9A and 9B illustrate a modified version of the device of FIGS. 7A to 7D. In most circumstances it is expected that the patients will collect their own faecal specimens using the dipstick, which will be returned, within its sheath, to a health professional for test development. As previously indicated in the description of FIG. 7, the sheath will preferably also be the test housing.

A modified version of the FIG. 7 test format, suitable for most markets, is shown in FIG. 9B. As distinct from the format illustrated in FIG. 7, in this modified version the test reagent is added to a reagent pad situated on the dipstick, instead of on the test strip. It should be noted that in this modified version, the amount of faecal specimen tested, and hence the test sensitivity, is controlled by the gap width between the upper and lower protective membranes. This can be set and controlled during manufacture for optimal test performance. This format of the device is intended for faecal specimen smearing by the patient and subsequent test development by the health professional. In this case, the dipstick would be smeared by the patient and inserted in the test housing for return for test development. For this format, a test kit would comprise: one test housing and dipstick, and one transport envelope (optional), issued to the patient; and bulk packaged test strips (desiccated), and a dropper bottle of buffer, issued to the laboratory/health professional for test development.

In the test method using this format, the patient smears the dipstick with faecal specimen, and then inserts the wiped dipstick into the housing (sheath) and returns them (in the transport envelope) for development. The laboratory/health professional opens the test housing, inserts the keyed test strip in the recess of the left hand panel, adds the specified number of drops of reagent to the reagent pad of the dipstick, and then seals the test housing closed and reads the result through the window in the standard manner.

For situations where the smearing of the dipstick and test development is done at the same site, e.g. by the laboratory/health professional or by the test subject for home testing, the test housing may be manufactured and issued with the test strip in place.

In this format, a test kit would consist of a test housing, issued in a desiccated pouch, and a dipstick. The test procedure would require the operator to smear and wipe the dipstick and insert it into the test housing. The test would be initiated by addition of reagent to the dipstick as already described.

In some markets, e.g. in Japan, the patient may be unwilling to smear his or her faecal specimen on the dipstick collection device, preferring instead to present the faecal specimen directly to the laboratory or health professional for testing. In addition, the Japanese diet causes many false positives with guaiac testing, making specific immunodiagnostic testing the only viable option.

A number of different formats of the device of the present invention are particularly suitable for immunodiagnostic testing in this market.

Firstly, a sheathed dipstick collection device of the type illustrated in FIG. 10 may be used as it is quite inexpensive and therefore suitable for mass-screening programs. In use, such a collection device is dipped into the faecal specimen so that faecal material contacts the absorbent matrix through the opening in the sheath, and the dipstick collection device is then removed with the sheath being discarded into the specimen container. The dipstick device having the sample applied can then be inserted into a protective cover member provided with one or more ports or openings for addition of test reagent, as well as one or more reading windows, so that the appropriate test reagent can be added and the test result read with the dipstick device in situ within the protective cover member. (Alternatively, the protective cover member could have the test reagent sealed in the base and the dipstick device could, on insertion, perforate a frangible seal to automatically release the reagent and initiate test development.) In another option, the dipstick device having the sample applied may be inserted into a transparent tube or the like as a protective cover member with test reagent already present or being added to the tube prior to insertion of the dipstick device.

Alternatively, a hybrid guaiac/immunodiagnostic test is also possible. In this hybrid test, a guaiac dipstick collection device, as already described, would have a band or spot of antibody specific for human haemoglobin immobilised within the guaiac paper. Typically, the antibody would be coated on latex beads of a size sufficient to prevent their migration within the guaiac paper. Addition of developer to one margin of the guaiac paper would cause migration of collected sample across the paper and the specific accumulation of human haemoglobin at the antibody band or spot. The guaiac developer would indicate this accumulation by a concentrated colour development in the region of the antibody. The use of an antibody in such a hybrid test would require that the dipstick should be issued in a desiccated package (to protect the antibody), and that the test should be developed soon after faecal addition, in order to prevent degradation of the antibody.

3. Combined Guaiac/Immunodiagnostic Testing

For cost-effective, mass-screening program for detection of faecal occult blood in at-risk populations (e.g. 50 years and older), a combined guaiac/immunodiagnostic test is also feasible which allows guaiac positives to be confirmed by an immunodiagnostic format, (see Allison et al., 1996, supra). In such a combined test, for example using the device described in FIGS. 9A and 9B, the dipstick collection device may be provided with a guaiac absorbent matrix or one side of the elongate carrier and a second absorbent matrix on the opposite side of the carrier for collection of sample material for immunodiagnostic testing. The protective cover member provides a sheath or housing for transport of the dipstick collection device, and in addition may be configured as previously described to provide a test housing with ports or windows for addition of test reagent and reading of test results in the guaiac test. In use, the dipstick collection device is dipped into a faecal sample thereby collecting sample material on both sides, and excess material is then wiped off prior to insertion of the collection device into the protective cover member.

Testing of the collected samples by the laboratory or health professional may then simply comprise carrying out of guaiac testing on one side of the dipstick device in situ in the protective cover member as a test housing, and where confirmation of a guaiac positive result is required, elution of the specimen from the absorbent matrix on the other side of the device by addition of buffer, with the eluted specimen being transferred directly onto an immunochromatographic test strip as described in Australian Patent Application No. 21852/92, above.

Such a combination guaiac/immunodiagnostic test offers significant advantages in that it allows two types of tests on the same faecal specimen, and thus enables direct immunodiagnostic confirmation of a guaiac-positive test result. In particular, it provides a system for cost-effective mass screening of at risk populations in which a guaiac screen can be carried out without dietary restriction and as described above guaiac-positive results can be confirmed by an immunodiagnostic procedure on the same specimen.

With test kits as described above, immunochromatographic testing may be rendered sufficiently inexpensive as to be feasible for developing countries, as the dipstick collection device may be mass produced using very high speed, low-cost manufacturing procedures; the sheath serves both for transfer of the dipstick collection device to the test site and also as the base and instruction card for the test itself (this rationalises material usage and kit complexity); the test strips, through bulk packaging in a desiccated container, avoid the usual expensive requirement for individual desiccated packaging in a foil pouch; and the minimal size and number of test components ensures the inexpensive packaging, storage and transport costs.

What is claimed is:

1. A sample collection device comprising:
   (a) a collection member which comprises an elongate dipstick having at least one absorbent matrix affixed to the dipstick, and
   (b) a substantially planar protective housing for said collection member, said protective housing being separate from said collection member and said collection member being removable and replaceable with respect to said protective housing, said protective housing comprising first and second substantially planar panels in overlying relationship which are joined to define an elongate internal recess between said panels, said internal recess being adapted to receive at least the absorbent matrix of said collection member when the collection member is assembled therewith,
   wherein said protective housing is provided with at least one window extending through a panel thereof into said internal recess, the window being located so that it corresponds with at least a portion of an absorbent matrix when the collection member is assembled within the protective housing.

2. A device according to claim 1 wherein said dipstick comprises a material selected from the group of plastics materials, water-proofed cardboard and water-resistant cardboard.

3. A device according to claim 1 wherein said dipstick comprises a transparent or translucent material.

4. A device according to claim 1 wherein said internal recess in said housing receives substantially the entire length of said collection member.

5. A device according to claim 1 wherein said protective housing comprises a water-impervious non-absorbent material selected from plastics materials, water-proofed cardboard, water-resistant cardboard and laminated materials.

6. A device according to claim 1 further comprising a removable, sealing layer covering the window in the protective housing.

7. A device according to claim 1 wherein the protective housing is provided with at least one additional window through a wall thereof, said additional window located so that, in conjunction with the use of a collection member that is at least partially transparent, the additional window provides an aperture for reading the results of a test conducted by the device.

8. A device according to claim 1 wherein the protective housing further comprises at least one test reagent sealed therein with a frangible seal, whereby said frangible seal may be broken when said collection member is inserted into the protective housing.

9. A device according to claim 1 wherein said protective housing comprises:
   a first opposable component adapted to receive said collection member, and
   a second opposable component,
wherein said first and second opposable component can be brought into opposition.

10. A device according to claim 1 wherein at least a portion of the absorbent matrix is impregnated with guaiac.

11. A device according to claim 1 wherein said collection member comprises a plurality of absorbent matrices, and at least a portion of one of said matrices is impregnated with guaiac.

12. A device according to claim 1 further comprising a test strip comprising means for detecting an analyte in a sample.

13. A device according to claim 1, wherein said protective housing is a sheath having a generally flat, planar shape.

14. A device according to claim 1, wherein said protective housing is a single piece sheath having a generally flat shape.

15. A device according to claim 1, wherein said protective housing is a flexible sheath.

16. A device according to claim 1 wherein said absorbent matrix comprises an absorbent material selected from the group of filter paper, cellulose, nitrocellulose, nylon, rayon, glass fiber, sintered glass, fleece and non-woven synthetic materials and porous synthetic materials.

17. A device according to claim 16 wherein said absorbent material is filter paper.

18. A device according to claim 1 wherein the absorbent matrix comprises a sample collection matrix in fluid communication with an absorbent reagent matrix, wherein reagent added to the absorbent matrix can flow along the collection member and into the sample collection matrix.

19. A device according to claim 18 wherein at least the region of the junction between said sample collection matrix and said absorbent reagent matrix is covered with an impervious protective layer to prevent contamination of the absorbent reagent matrix when a sample is applied to the sample collection matrix.

20. A device according to claim 1 wherein the absorbent matrix comprises a sample collection matrix in fluid communication with a capillary means, wherein reagent added to the absorbent matrix can flow along the collection member and into the sample collection matrix.

21. A device according to claim 20 wherein at least the region of the junction between said sample collection matrix and said capillary means is covered with an impervious protective layer to prevent contamination of the capillary means when a sample is applied to the sample collection matrix.

22. A device according to claim 1 wherein said collection member is at least partial covered with a protective cover layer.

23. A device according to claim 22 wherein said protective cover layer is removable.

24. A device according to claim 22 wherein said protective cover layer has at least one window exposing at least a portion of said absorbent matrix.

25. A device according to claim 24 wherein a filter material is located over the exposed portion of the absorbent matrix.

26. An assay device for detection and/or determination of an analyte in a sample, comprising:
   (a) a collection member comprising an elongate dipstick having at least one absorbent matrix affixed to the dipstick,
   (b) a substantially planar protective housing for said collection member, said protective housing being separate from said collection member and said collection member being removable and replaceable with respect to said protective housing, said protective housing comprising first and second substantially planar panels in overlying relationship which are joined to define an elongate internal recess between said panels, said internal recess being adapted to receive at least the absorbent matrix of said collection member when the collection member is assembled therewith, and
   (c) means to detect an analyte in a sample collected with said collection member,
      wherein said protective housing is provided with at least one window extending through a panel thereof into said internal recess, the window being located so that it corresponds with at least a portion of an absorbent matrix when the collection member is assembled within the protective housing.

27. An assay device according to claim 26, wherein said means to detect said analyte comprises guaiac impregnated in at least a portion of the absorbent matrix.

28. A device according to claim 26, wherein said protective housing is a sheath having a generally flat, planar shape.

29. A device according to claim 26, wherein said protective housing is a flexible, single piece sheath having a generally flat shape.

30. An assay device according to claim 26, wherein said means to detect said analyte comprises a test strip for detecting said analyte in said sample.

31. An assay device according to claim 30 wherein said test strip further comprises a chromatographic medium.

32. An assay device according to claim 30, wherein said test strip is adapted to be located on said collection member.

33. An assay device according to claim 30 wherein said test strip is adapted to be joined to said protective housing.

34. An assay device according to claim 33 wherein said protective housing further comprises:
   a first opposable component adapted to receive said collection member, and
   a second opposable component,
said test strip adapted to be joined to said second opposable component, and said first and second opposable components can be brought into opposition so as to cause the sample to be brought into contact with said test strip.

35. A sample collection device comprising:
   (a) a collection member which comprises an elongate dipstick having a first section and a second section, said second section comprising a substantial portion of the length of the elongate dipstick,
   (b) at least one absorbent matrix affixed to the first section of the dipstick, and
   (c) a protective housing for said collection member, said collection member being removable and replaceable from said protective housing, the protective housing having an internal recess adapted to receive said collection member when the collection member is assembled therewith,
      wherein said protective housing is provided with at least one window extending through a wall thereof, the window being located so that it corresponds with at least a portion of the absorbent matrix when the collection member is assembled within the protective housing, the protective housing masking the second section of the collection member.

* * * * *